United States Patent [19]

Li

[11] 4,005,584
[45] Feb. 1, 1977

[54] COMPOSITION, METHOD AND APPARATUS FOR ABSORPTION HEATING

[75] Inventor: Chien C. Li, Williamsville, N.Y.

[73] Assignee: Allied Chemical Corporation, Morris Township, N.J.

[22] Filed: Apr. 10, 1975

[21] Appl. No.: 567,043

[52] U.S. Cl. .................................................. 62/112
[51] Int. Cl.$^2$ ........................................ F25B 15/00
[58] Field of Search ............... 252/67, 69, 170, 175; 260/347.3, 347.4, 347.5, 347.8; 62/112

[56] References Cited

UNITED STATES PATENTS

| | | | |
|---|---|---|---|
| 2,040,898 | 5/1936 | Zellhoefer | 252/69 |
| 2,040,901 | 5/1936 | Zellhoefer | 252/69 |
| 2,040,902 | 5/1936 | Zellhoefer | 252/69 |
| 2,040,905 | 5/1936 | Zellhoefer | 252/69 |
| 2,040,909 | 5/1936 | Zellhoefer | 252/69 |
| 2,594,272 | 4/1952 | Kauck et al. | 252/67 |
| 3,643,455 | 2/1972 | Hensel, Jr. et al. | 62/112 |

*Primary Examiner*—Lloyd L. King
*Attorney, Agent, or Firm*—Anthony J. Stewart; Ernest D. Buff

[57] ABSTRACT

The invention comprises absorption pair compositions consisting essentially of selected lower alkyl fluorocarbon solutes dissolved in selected furan ring containing absorbents. The invention further comprises a method of absorption heating utilizing such compositions and absorption heating apparatus incorporating such compositions. The invention also comprises a novel furan compound, namely, n-butyl tetrahydrofurfuryl ether.

14 Claims, No Drawings

COMPOSITION, METHOD AND APPARATUS FOR ABSORPTION HEATING

This invention relates to a method of absorption heating, a novel absorption pair for utilization in the method and an improved absorption heating apparatus.

In view of diminishing fossil fuel supplies, and hence, increasing fuel costs, there is a need to minimize the amount of fuel society consumes to heat habitable space.

The heat pump concept, wherein available energy is taken from an ambient source such as outside air, and combined with fuel energy to heat space, is not new. Existing concepts include electrically driven-vapor compression heat pumps and absorption heat pumps. The latter require an absorption pair which comprises a solvent and a solute wherein the solvent remains a liquid, which may be a solution, throughout the operation of the apparatus, and the solute having a liquid and vapor phase in the cycles of the operation. The solute must be soluble in the solvent and must be readily separable as a vapor from the solvent by means of evaporation. In addition, the solute must be suitable for condensation from the vapor back to a liquid form. In general, all absorption heating apparatus require essentially the same parts and function in essentially the same way regardless of the particular solute and solvent used. The major components of the apparatus are a generator, condenser, evaporator, absorber and absorption pair. The solute passes through all units and the solvent, sometimes also known as the absorbent, is confined to movement through the generator and absorber.

In operation, a mixture of absorbent and solute is heated in the generator to boil off most of all of the solute which rises as a vapor through a connecting conduit to the condenser. The mixture may be heated in the generator by any suitable means such as a gas flame, geothermal heat, solar heat or warm water.

The generator and condenser operate at relatively high pressure, so the condensing temperature of the solute is sufficiently high to permit rejecting the latent heat emitted by the condensing solute to outside air or cooling water passing through or around the condenser.

The liquid solute leaving the condenser passes through a conduit to a throttling valve, through the throttling valve and through another conduit to the evaporator. The throttling valve throttles the liquid solute to a lower pressure so it will boil at a relatively low temperature in the evaporator and thus absorb heat from air or water passing through or around the evaporator.

The vaporized solute passes from the evaporator through a conduit to the absorber where heat of mixing is emitted as it is dissolved in cool absorbent which has been carried to the absorber by means of a conduit connecting the absorber with a generator outlet. The mixture of absorbent and solute resulting in the absorber then passes through a conduit to the generator where it is reheated to continue the process.

Any suitable material of construction for the apparatus may be used which can withstand the encountered temperature, pressure and corrosive properties, if any, of the solvent and solute. Such a heat absorption apparatus is particularly desirable since moving parts, if any, are minimal when compared with the moving parts found in electrically driven-vapor compression heat pumps.

Unfortunately, the known solute/solvent systems for heat pumps have serious disadvantages. The most common solute/solvent pair (absorber pair) is ammonia/water. The ammonia/water pair has a disadvantage since the heating efficiency of apparatus utilizing the ammonia/water absorber pair is not as high as desired; i.e. the coefficient of performance (COP) practically attainable is generally less than about 1.50 and at low generator temperature, i.e., below 180° F., and at high generator temperatures, i.e., above 220° F., is generally below about 1.3. COP is a measure of the efficiency of the absorption cycle and is the ratio of the heat output to the energy input. The ammonia/water combination has additional disadvantages. Water is highly volatile, thus preventing complete separation of the ammonia from the water in the generator at high generator temperatures. The condensing pressure required to condense the ammonia is undesirably high, thus requiring equipment capable of withstanding such pressure.

The only other commercial absorber pair is water/lithium bromide wherein water is used as the solute and lithium bromide is used as the absorbent. The water/lithium bromide absorber pair has undesirable characteristics. For example, water as a solute is limited to an evaporation temperature of above about 30° F., which is its freezing point. Lithium bromide is not sufficiently soluble in water to permit the absorber to be air cooled. The extremely low pressures in the system require large vapor conduits. Unless the system is precisely controlled, lithium bromide can crystallize and cause fouling of the system and the generator temperature cannot efficiently operate below 180° F. nor above 215° F. Additionally, aqueous lithium bromide solutions are corrosive, thus requiring special alloys for suitable apparatus.

Other absorber pairs which have been suggested have not been commercially accepted due to one or more disadvantages. Such disadvantages include a lack of sufficient affinity of the absorbent for the solute vapor, thus preventing sufficient absorption of the solute vapor to draw in and compress the solute. The absorber pairs have frequently not been mutually soluble over the whole range of operating conditions, thus permitting crystallization and the formation of solid particles which make it difficult or impossible for proper fluid circulation. The absorbent has frequently been volatile, thus preventing the refrigerant vapor leaving the generator from being pure. When absorbent evaporates from the generator, the efficiency of the system is frequently substantially reduced since energy input is wasted in evaporation. Additionally, the absorbent pairs previously suggested are frequently unstable, cause corrosion of the apparatus, are toxic or are highly flammable. Absorption pairs suggested in the prior art frequently have unacceptably high or unacceptably low working pressures. The working pressures should be as near to atmospheric pressure as possible to minimize equipment weight and minimize leaking into or out of the system. In addition, pressure difference between the high side and low side is frequently too high to facilitate circulation of the solution. The solutes suggested in the prior art frequently have a latent heat of evaporation which is unacceptably low, thus requiring large quantities of fluids to be circulated and the coefficient of performance of other absorber pairs suggested in the prior art is usually too low for serious consideration in commercial apparatus.

BRIEF DESCRIPTION OF THE INVENTION

In accordance with this invention, there is provided a method and apparatus for absorption heating and a novel absorber pair for absorption heating which has a high coefficient of performance, has good stability, causes little corrosion, has a relatively high flash point, operates at approximately atmospheric pressure and has low toxicity. The high coefficient of performance is due to a strong affinity between the solute and solvent, good mutual solubility at absorber conditions and ease of separation at generator conditions, good absorbent volatility and a solute having a high latent heat of vaporization. The method of absorption heating comprises absorbing a lower alkyl fluorocarbon solute selected from the group consisting of dichloromonofluoromethane, monochlorodifluoromethane, trifluoromethane, and monochloromonofluoromethane in a furan ring containing solvent to release heat of solution in the vicinity of an area to be heated, heating the resulting solution to release the lower alkyl fluorocarbon from the solvent, condensing the released lower alkyl fluorocarbon to form liquid lower alkyl fluorocarbon, evaporating the liquid lower alkyl fluorocarbon at a location removed from the vicinity of the area to be heated, and returning the evaporated lower alkyl fluorocarbon to the vicinity of the area to be heated for reabsorption into the solvent. Also in accordance with this invention, there is provided a novel furan compound, namely, n-butyl tetrahydrofurfuryl ether, which finds special utility when used as a component of the novel absorption pairs of this invention.

In general, in accordance with this invention, the solvent used in the absorption pair is an assymetrical furan ring containing compound having a boiling point between about 140° and 250° C. The compound has the generic formula

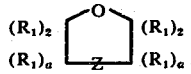

wherein $R_1$ is independently at each occurrence H; lower alkyl; lower alkoxy; phenyl; lower alkylene phenyl; hydroxy containing lower alkyl; lower alkyl carboxy; alkoxy alkyl of from 2 through 6 carbon atoms; lower alkylene carboxylate of from 2 through 6 carbon atoms; fluorine or chlorine; $a$ is independently at each occurrence an integer of 1 or 2; and Z is a single or double bond; provided that, when Z is a single bond, $a$ is 2, when Z is a double bond, $a$ is 1, and provided that the compound contains at least one $R_1$ group having an oxygen atom which has a single bond to a carbon atom.

The solvents are preferably selected from methyltetrahydrofurfuryl ether, ethyltetrahydrofurfuryl ether, propyl tetrahydrofurfuryl ether, butyltetrahydrofurfuryl ether and methyl-2,5-dihydro,2,5-dimethoxy-2-furan carboxylate.

The new and useful compositions of matter for use in accordance with the invention comprises from about 4 to about 60 weight percent of a lower alkyl fluorocarbon selected from the group consisting of monochlorodifluoromethane, dichloromonofluoromethane, trifluoromethane, and monochloromonofluoromethane dissolved in one of the above assymetrical furan ring containing compounds by weight of such compound. When the fluorocarbon is dichloromonofluoromethane, the furan ring containing compound, however, is not

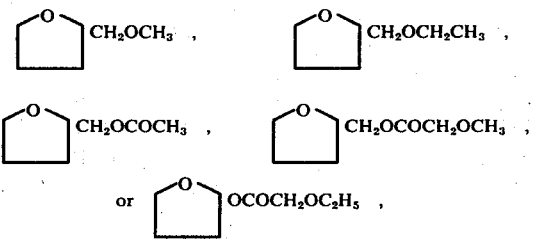

since the combination of dichloromonofluoromethane and these furan compounds are known prior art compositions (U.S. Pat. No. 2,040,902) generally disclosed for use in absorption refrigeration without any indication of their efficiency in either absorption refrigeration or absorption heating. Three of the above compositions contain double bonded oxygen atoms, and, while being acceptable compositions for use in the invention under the generic disclosure, are not preferred due to increased instability resulting from the double bonded oxygen atom. It has now been found that these compositions are unexpectedly highly efficient in a method and apparatus for absorption heating.

The preferred compositions for use in conjunction with the method and apparatus of the invention comprise:
  from about 4 to about 60 weight percent of dichloromonofluoromethane dissolved in n-butyl tetrahydrofurfuryl ether based on the weight of n-butyl tetrahydrofurfuryl ether;
  from about 4 to about 60 weight percent of dichloromonofluoromethane dissolved in methyl-2,5-dihydro,2,5-dimethoxy-2-furan carboxylate based on the weight of methyl-2,5-dihydro,2,5-dimethoxy-2-furan carboxylate;
  from about 4 to about 60 weight percent of a lower alkyl fluorocarbon selected from the group consisting of monochlorodifluoromethane, trifluoromethane and monochloromonofluoromethane dissolved in a furan ring containing solvent selected from methyltetrahydrofurfuryl ether, ethyl tetrahydrofurfuryl ether, propyltetrahydrofurfuryl ether, n-butyl tetrahydrofurfuryl ether and methyl-2,5-dihydro,2,5-dimethoxy-2-furan carboxylate based on the weight of such solvent.

The novel improved absorption apparatus of the invention comprises known prior art absorption heating apparatus components in conjunction with one of the foregoing lower alkyl fluorocarbon solutes in one of the foregoing furan ring containing solvents as the absorption pair.

DETAILED DESCRIPTION OF THE INVENTION

In general, in accordance with the method of this invention, the solvent used in the absorption pair is an assymetrical furan ring containing compound having a boiling point between about 140° and 250° C. The compound has the generic formula

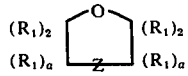

wherein $R_1$, $a$ and $Z$ are as previously defined and the compound contains at least one $R_1$ group having an oxygen atom which has a single bond to a carbon atom.

Lower alkyl, lower alkoxy, lower alkyl carboxy, or lower alkylene as used herein means alkyl, alkoxy or alkylene of from 1 through 5 carbon atoms. Examples of lower alkyl groups are -$CH_2CH_3$; -$CH_3$;

and -$CH_2CH_2CH_3$.

Examples of lower alkoxy groups are -$OCH_3$; -$OCH_2CH_3$ and

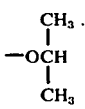

Phenyl groups are those groups containing a phenyl ring which is unsubstituted or substituted with methyl, ethyl, hydroxy, methoxy, ethoxy, methyl methoxy, fluorine or chlorine. Examples of phenyl groups are

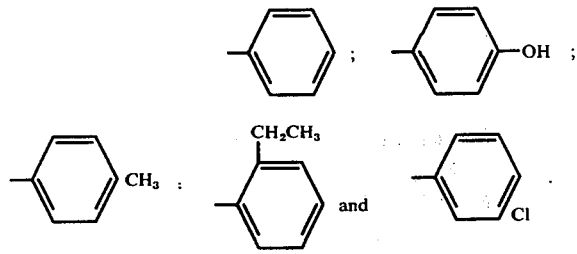

Lower alkylene phenyl groups are phenyl groups connected to the furan ring by a lower alkylene group. Examples of such groups are

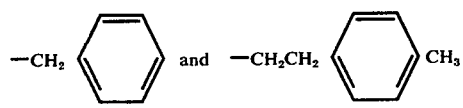

Examples of hydroxy containing lower alkyl groups are -$CH_2OH$; -$CH_2CH_2OH$ and

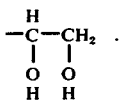

Examples of lower alkyl carboxy groups are -COOH; -$CH_2COOH$ and -$CH_2CH_2COOH$.

Examples of alkoxy alkyl groups, i.e., those containing 2 to 6 carbon atoms, are -$CH_2OCH_3$; -$CH_2OCH_2CH_3$; -$CH_2OCH_2CH_2CH_3$; -$CH_2OCH_2CH_2CH_2CH_3$ and -$CH_2CH_2OCH_3$. Preferred alkoxy alkyl groups are those containing either 5 or 6 carbon atoms due to higher efficiency at high generator temperature and due to increased stability, those alkoxy alkyl groups wherein the intermediate alkyl portion, i.e. that portion attached to the furan ring contains 2 to 3 carbon atoms. When the intermediate alkyl group is ethyl the furan ring compound unexpectedly exhibits improved solubility for the fluorocarbon.

Examples of lower alkylene carboxylate groups, i.e., those containing 2 to 6 carbon atoms, are -$CH_2$-$COOCH_3$;

$$\text{and} \quad -CH_2-\underset{\underset{CH_3}{|}}{\overset{\overset{CH_3}{|}}{C}}-COOCH_3 \ .$$

It is theorized that the boiling point of the simple furan ring is increased by adding an alkyl or an alkoxy group to the furan ring to form an asymetrical molecule. The added group should preferably permit an increase in the negative charge on the furan ring oxygen atom.

The furan ring containing compounds employed in the present invention are usually characterized by high flash points which reduce the flame hazard when they are used.

Asymetrical as used in relation to the furan ring containing compound means either that at least one of the $R_1$ groups at the 2 position on the furan ring is different from both of the $R_1$ groups at the 5 position or at least one of the $R_1$ groups at the 3 position is different from both of the $R_1$ groups at the 4 position. In the preferred furan ring compounds, at least one of the $R_1$ groups at the 2 position is different from both of the $R_1$ groups at the 5 position.

Alkyl as used above means an aliphatic hydrocarbon radical in which the hydrogens may be wholly or partially substituted by fluorine or chlorine.

The compound should preferably contain at least one $R_1$ group having an oxygen atom which is bonded on one side to a carbon atom and is bonded on the other side to either a carbon atom or a hydrogen atom. At high generator temperatures, carboxy groups, particularly free rather than esterified carboxy groups should be avoided since such groups tend to increase the corrosiveness of the compound and tend to decompose more rapidly than other groups. Carboxy groups are, however, suitable for compounds which will be used at low generator temperatures, i.e., below 225° C. The more preferred $R_1$ groups are those containing an alcohol or ether oxygen atom.

The foregoing furan ring containing compounds may be prepared by known procedures. Detailed discussions of the chemistry of furan and its derivatives are found in Chapter 4 of *Heterocyclic Compounds Volume I*, edited by Robert C. Elderfield, Wiley and Sons, Inc., 1950 and at pages 377 through 490 of *Advance in Heterocyclic Chemistry Volume 7*, edited by A. R. Katritzky and A. J. Boulton, Academic Press 1966.

A general method for preparation of furan ring containing compounds which are suitable for use in accordance with this invention is as follows:

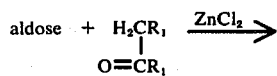

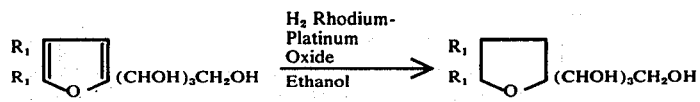

where $R_1$ is independently at each occurrence any group as previously defined. $R_1$ may be carbonyl or carboxy; however, these groups will be reduced to alcohol groups upon hydrogenation. Such reduced groups may, however, be subsequently oxidized to a carbonyl or carboxyl group with a strong oxidizing agent such as $KMnO_4$, lead acetate or $HIO_4$.

Another general method for the preparation of furan ring containing compounds which are suitable for use in accordance with this invention is by ring formation from the enol form of a 1–4 carbonyl compound.

Again, $R_1$ may be any group as previously defined; however, since carbonyl and carboxyl groups may be reduced during hydrogenation such groups are generally preferably obtained by utilizing a suitable hydroxy alkyl (alkanol) group and oxidizing the hydroxy alkyl group to the desired carbonyl or carboxyl group subsequent to hydrogenation.

Some specific suitable furan ring containing compounds and their methods of preparation are as follows: A suitable catalyst for reduction of the furan ring to the tetrahydrofuran ring is a platinum oxide-rhodium catalyst.

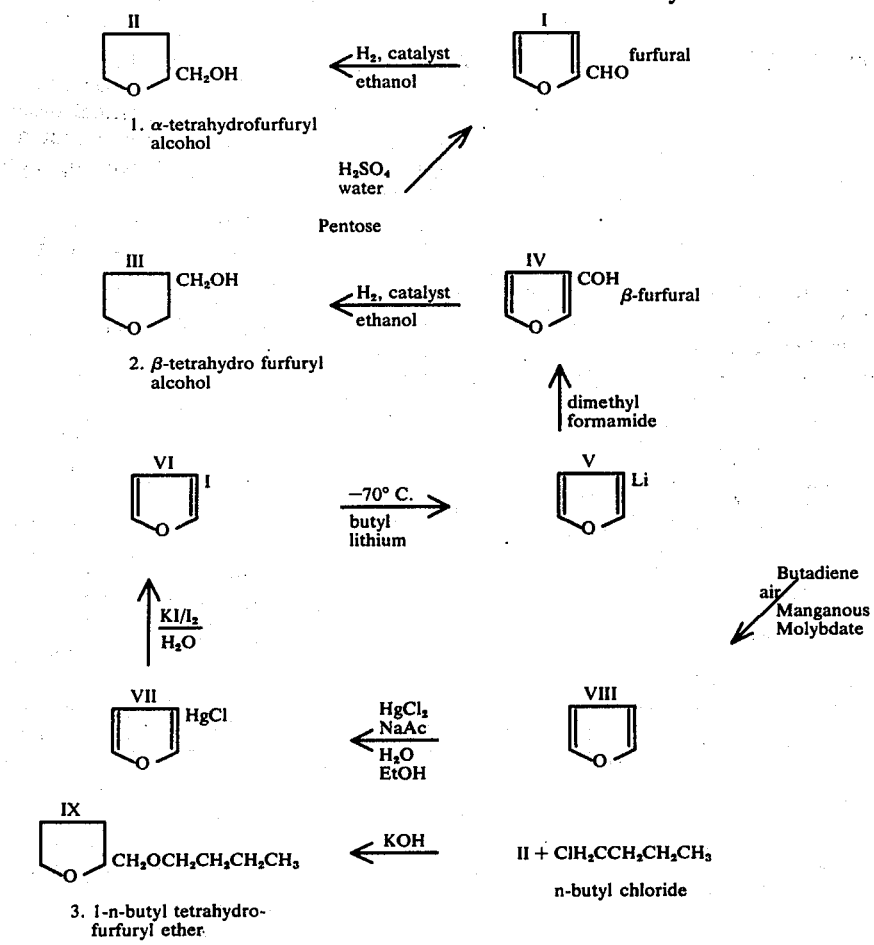

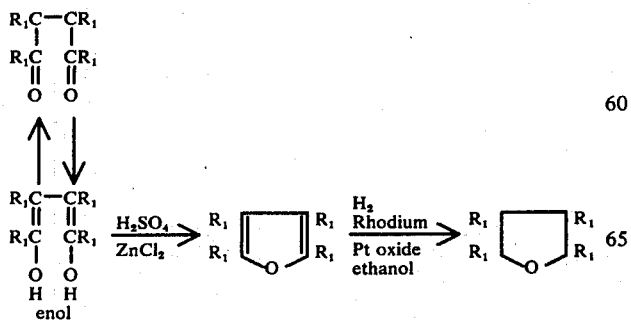

This compound, which forms a part of this invention, exhibits properties, when used in absorption pairs, which are unexpected over the prior art ethyl homolog. Prior to this invention, there existed no reason to expect the butyl compound to be so much more efficient in an absorption pair than the ethyl compound of the prior art.
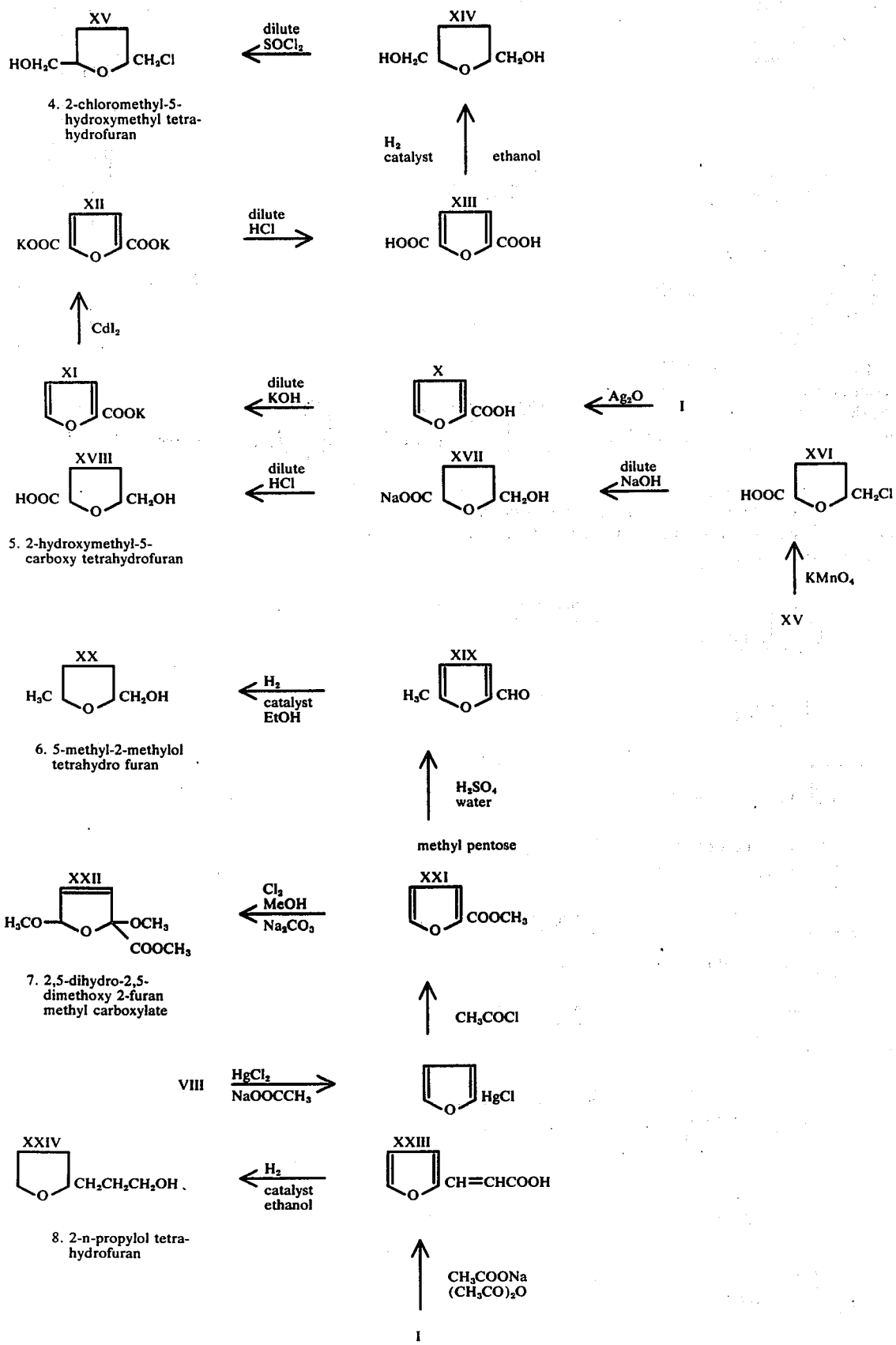

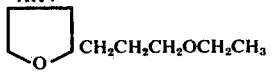 

9. 2-n-propyl ethoxy tetrahydrofuran

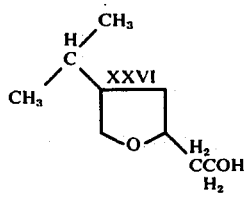 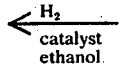 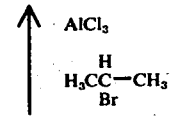

10. 2-ethylol-4-isopropyl tetrahydrofuran

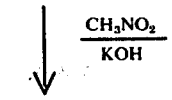

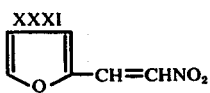 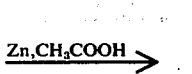 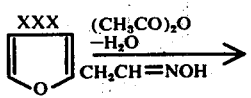 

Examples of other suitable furan ring containing compounds which can be prepared in accordance with known methods are:

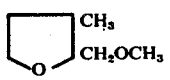 2-methoxymethyl-3-methyl tetrahydrofuran

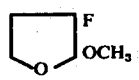 2-methoxy-3-fluoro tetrahydrofuran

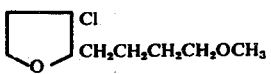 2-methoxy n-butyl-3-chloro tetrahydrofuran

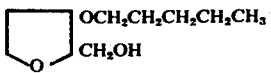 2-methylol-3-n-pentoxy tetrahydrofuran

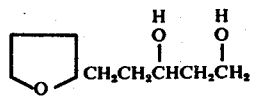 2-[3,5-hydroxy n-pentyl] tetrahydrofuran

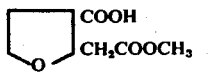 tetrahydro-3-carboxy-2 furan methyl acetate

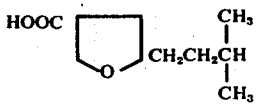 2-[3,3-dimethyl propyl]-4-carboxy tetrahydrofuran

 2,3-dicarboxy-4-methyl tetrahydrofuran

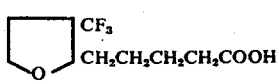 tetrahydro-3-trifluoro-methyl-2-n-pentanoic acid

-continued

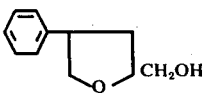
2-methylol-4-phenyl tetrahydrofuran

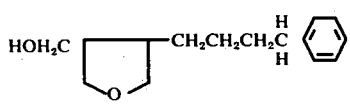
3-[4-phenyl butylene]-4-methylol tetrahydrofuran

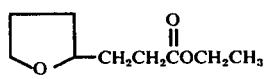
tetrahydro-2-furan ethyl propionate

The solute used in the absorption pair is a fluorinated methyl group which contains at least one carbon atom. The methyl group preferably also contains at least one hydrogen atom and at least one chlorine atom and is assymetrical. It is believed that the presence of the chlorine atom and the assymetrical character of the methyl group permits a more positive charge to form on the hydrogen atom, thus increasing the affinity of the hydrogen atom for the electronegative oxygen atom in the furan ring of the solvent.

The preferred absorption pair for use in accordance with the invention comprises a compound selected from the group consisting of dichloromonofluoromethane, monochlorodifluoromethane, trifluoromethane and monochloromonofluoromethane dissolved in a furan ring containing solvent selected from 2-methyltetrahydrofurfuryl ether, 2-ethyl tetrahydrofurfuryl ether, 2-propyl tetrahydrofurfuryl ether, 2-butyl tetrahydrofurfuryl ether and methyl 2,5-dihydro-2,5-dimethoxy-2-furan carboxylate.

Those absorption pairs unexpectedly have very high efficiency at high generator temperatures, when the solvent is n-butyl tetrahydrofurfuryl ether. For example, at a generator temperature of 370° F., a COP of about 1.60 can be obtained using n-butyl tetrahydrofurfuryl ether and dichloromonofluoromethane as the absorption pair whereas when ethyl tetrahydrofurfuryl ether is used in conjunction with dichloromonofluoromethane at 370° F., a COP of about 1.58 is obtained which, while indicating a very high efficiency, is about 3.5 percent less efficient in heating improvement than when the n-butyl tetrahydrofurfuryl ether is used. In calculating the comparative COP's between the butyl and the ethyl solvents, an evaporator temperature of 45° F., a condenser temperature of 120° and an absorber temperature of 125° F. are assumed. Under these conditions, the efficiencies for the butyl and ethyl solvents are highest between about 325° and about 400° F. and are maximized at the 370° F. generator temperature. When methyl tetrahydrofurfuryl ether is used as the solvent under the foregoing conditions, the system is inoperative due to evaporation of the methyl solvent from the generator. When the generator temperature is lowered at the same evaporator, condenser and absorber temperatures, the maximum COP obtainable when the methyl solvent is used is about 1.57. The preferred absorption pair composition when ethyl or butyl absorbents are used is from about 10 to about 60 weight percent of fluorocarbon, preferably dichloromonofluoromethane, by weight of absorbent.

Similarly, the system employing ammonia as the solute and water as the solvent cannot be operated at either high generator temperatures or at low generator temperatures and the maximum COP practically obtainable with the ammonia and water system at any generator temperature is about 1.5.

Those absorption pairs wherein the solvent is methyl 2,5-dihydro-2,5-dimethoxy-2-furan carboxylate can be used at high generator temperatures but only at low COP values; however, those pairs wherein the solvent is the carboxylate, unexpectedly have higher COP values at low generator temperatures than any other known absorption pair. For example, at an evaporator temperature of 45° F., a condenser temperature of 125° F. and an absorber temperature of 125° F., the COP of a system using dichloromonofluoromethane and methyl 2,5-dihydro-2,5-dimethoxy-2-furan carboxylate would be about 1.4 at a generator temperature of 370° F., but would be about 1.5 at the very low generator temperature of 160° F. No other known absorption pair would have a COP as high as about 1.5 at a generator temperature of 160° F. under the same conditions.

The preferred absorption pair composition when the 2,5-dihydro-2,5-dimethoxy-2-furan carboxylate absorbent is used is from about 10 to about 60 weight percent fluorocarbon, preferably dichloromonofluoromethane, by weight of absorbent.

When methyl 2,5-dihydro-2,5-dimethoxy-2-furan carboxylate is used, the preferred temperature to which the solution is heated in the generator is preferably between about 150° and 300° F. and most preferably between about 160° and about 210° F. Such low generator temperatures are particularly suitable for low temperature heat sources such as solar energy.

The preferred fluorocarbon solute for use in accordance with the method of the invention is dichloromonofluoromethane due to its stability and desirable vaporization temperature at or near atmospheric pressure.

In general, all of the foregoing fluorocarbon solutes have been found to be suitable solutes over a broad range of generator temperatures for the release of solute. Acceptable generator temperatures for use with these fluorocarbons range from about 150° to about 425° F. Dichloromonofluoromethane is generally the preferred solute for use over this temperature range since a higher COP is usually obtained. The remaining foregoing fluorocarbons are, however, preferred in special applications, for example, when lower evaporator temperatures are desired.

The higher generator temperatures, i.e., from about 250° to about 425° F. result in higher COP's. Highest temperatures generally result in undesirable decomposition. The most preferred generator temperature to retain high COP's and low decomposition is from about 300° to about 350° F. The lower generator temperatures are used when low temperature heat sources such as solar heat are to be used to heat the generator.

The temperature at which the absorption of the solute into the solvent occurs is preferably from about 90° to about 130° F. A large percentage of the heat released in absorption heating occurs when heat of mixing is released during absorption of the solute by the solvent and the heat of mixing released is higher at a lower absorption temperature. The temperature of the absorption is; however, limited by the temperature of the area to be heated since the absorber provides heat to, and is cooled at the temperature of, such area.

The fluorocarbon solute, e.g., dichloromonofluoromethane is preferably evaporated at between about −5° and about 50° F. The most preferred evaporation temperature is between about 35° and 50° F. to avoid problems of excess condensation and ice formation at the evaporator.

The absorption heating apparatus of the invention, as previously discussed, comprises known absorption heating apparatus components in conjunction with the absorption pairs disclosed for use in the novel absorption heating method.

EXAMPLE 1

An absorption pair, consisting of 40 weight percent dichloromonofluoromethane solute in methyltetrahydrofurfuryl ether solvent by weight of solvent, is introduced into an absorption heating apparatus consisting essentially of a generator, condenser, evaporator and absorber. The condenser is cooled with water to maintain a temperature of 125° F. in the condenser and absorber, and a gas flame is provided under the generator to obtain a generator temperature of 300° F. A throttling valve is provided between the condenser and evaporator which is adjusted to maintain an evaporator temperature of 45° F. and a high pressure in the generator and condenser and a low pressure in the evaporator and absorber. In example 1, the generator and condenser is 60.2 p.s.i.a. and the pressure in the evaporator and absorber is 13.8 p.s.i.a. The heat or energy input provided by the gas flame is calculated by determining the volume of gas burned and multiplying by the calories provided per unit volume of burned gas. The heat output is determined by measuring the temperature rise in a known volume of water which is recycled around the condenser and absorber. The COP for the absorption system is calculated to be 1.544 indicating a very high efficiency.

EXAMPLE 2

Example 1 is repeated except ethyltetrahydrofurfuryl ether is substituted for methyl tetrahydrofurfuryl ether. The COP is calculated to be 1.540.

EXAMPLE 3

Example 1 is repeated except butyltetrahydrofurfuryl ether is substituted for methyl tetrahydrofurfuryl ether. The COP is calculated to be 1.514.

EXAMPLE 4

Example 1 is repeated except a saturated solution of ammonia in water at 125° F. at absorber pressure is used as the absorption pair. The COP is calculated to be only 1.243 which is low compared to the systems of the invention illustrated in examples 1, 2 and 3.

EXAMPLE 5

Example 1 is repeated except the generator temperature is increased to 350° F. The COP is calculated to be 1.572.

EXAMPLE 6

Example 2 is repeated except the generator temperature is increased to 350° F. The COP is calculated to be 1.577.

EXAMPLE 7

Example 3 is repeated except the generator temperature is increased to 350° F. The COP is calculated to be 1.582 which is a higher COP than is obtainable from any known absorption system which is not operated at extremely low pressures requiring expensive apparatus to handle the vacuum.

EXAMPLE 8

An attempt to repeat example 4 at a generator temperature of 350° F. is found to be impractical since generator pressures required to prevent vaporization of the water solvent in the ammonia/water system are unacceptably high.

EXAMPLE 9

Example 1 is repeated except methyl 2,5-dihydro-2,5-dimethoxy-2-furan carboxylate is substituted for methyl tetrahydrofurfuryl ether and the generator temperature is lowered to 160° F. The COP is calculated to be 1.5 which is a very high COP at such a low generator temperature. Such a system would be suitable for low temperature heat sources such as solar energy.

EXAMPLE 10

Preparation of n-butyl tetrahydrofurfuryl ether,

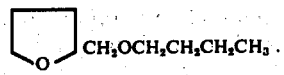

245 grams of tetrahydrofurfuryl and 230 grams of pulverized potassium hydroxide are stirred together in a 3 neck, 2 liter flask; equipped with a thermometer, stirrer, water condenser and back up trap; to form a slurry. 667 grams of n-butyl chloride is slowly added over a time period of fifteen minutes. The addition causes the temperature to rise from 24° to 59° C. The mixture is then heated to reflux at 88° C. for 2.5 hours, the mixture is cooled, filtered and refluxed with fresh potassium hydroxide for one hour. The mixture is again filtered and analysis by gas chromatography shows a 95% yield of n-butyl tetrahydrofurfuryl ether.

I claim:
1. The method of absorption heating which comprises:
   a. releasing heat of solution in the vicinity of an area to be heated by absorbing a compound selected from the group consisting of dichloromonofluoromethane, monochlorodifluoromethane, trifluoromethane and monochloromonofluoromethane in an assymetrical furan ring containing compound having a boiling point between about 140° and 250° C. and the generic formula

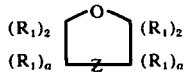

wherein $R_1$ is independently at each occurrence H; lower alkyl; lower alkoxy; phenyl; lower alkylene phenyl; hydroxy containing lower alkyl; lower alkyl carboxy; alkoxy alkyl of from 2 through 6 carbon atoms; lower alkylene carboxylate of from 2 through 6 carbon atoms; fluorine or chlorine, $a$ is independently at each occurrence an integer of 1 or 2; and Z is a single or double bond; provided that, when Z is a single bond, $a$ is 2, when Z is a double bond, $a$ is 1, and provided that the compound contains at least one $R_1$ group having an oxygen atom which has a single bond to a carbon atom, b. heating the resulting solution to release said fluorocarbon from said solvent, c. condensing released fluorocarbon to form liquid fluorocarbon, d. evaporating the liquid fluorocarbon at a location removed from the vicinity of the area to be heated, and e. returning the evaporated fluorocarbon to the vicinity of the area to be heated for reabsorption into said solvent.

2. The method of claim 1 wherein the furan ring containing compound is selected from the group consisting of methyltetrahydrofurfuryl ether, ethyltetrahydrofurfuryl ether, propyltetrahydrofurfuryl ether, butyltetrahydrofurfuryl ether and methyl-2,5-dihydro-2,5-dimethoxy-2-furan carboxylate.

3. The method of claim 2 wherein the fluorocarbon is dichloromonofluoromethane.

4. The method of claim 3 wherein the solvent is n-butyl tetrahydrofurfuryl ether.

5. The method of claim 4 wherein the solution is heated to from about 250° to about 425° F. to release dichloromonofluoromethane.

6. The method of claim 5 wherein said absorption takes place at a temperature of from about 90° to about 130° F.

7. The method of claim 6 wherein liquid dichloromonofluoromethane is evaporated at between about −5° and about 50° F.

8. The method of claim 5 wherein the solution is heated to from about 325° to about 400° F.

9. The method of claim 4 wherein from about 10 to about 60 percent of dichloromonofluoromethane by weight of n-butyl tetrahydrofurfuryl ether is used.

10. The method of claim 9 wherein the solvent is methyl-2,5-dihydro-2,5-dimethoxy-2-furan carboxylate.

11. The method of claim 10 wherein the solution is heated to from about 150° to about 300° F. to release dichloromonofluoromethane.

12. The method of claim 11 wherein the solution is heated to from about 160° to about 210° F.

13. The method of claim 10 wherein from about 10 to about 60 percent of dichloromonofluoromethane by weight of methyl-2,5-dihydro-2,5-dimethoxy-2-furan carboxylate is used.

14. The method of claim 1 wherein at least one of the $R_1$ groups contains an alcohol or ether oxygen atom.

* * * * *

UNITED STATES PATENT AND TRADEMARK OFFICE
CERTIFICATE OF CORRECTION

PATENT NO. : 4,005,584

DATED : February 1, 1977

INVENTOR(S) : Chien C. Li

It is certified that error appears in the above-identified patent and that said Letters Patent are hereby corrected as shown below:

Col. 18, line 21, "claim 9" should read --claim 3--.

Signed and Sealed this nineteenth Day of July 1977

[SEAL]

Attest:

RUTH C. MASON
Attesting Officer

C. MARSHALL DANN
Commissioner of Patents and Trademarks